United States Patent [19]

Katsu et al.

[11] Patent Number: 5,238,551
[45] Date of Patent: Aug. 24, 1993

[54] OXYGEN SENSOR

[75] Inventors: Masanori Katsu, Nagoya; Shigeharu Hashimoto, Okazaki, both of Japan

[73] Assignee: NGK Insulators, Ltd., Nagoya, Japan

[21] Appl. No.: 766,545

[22] Filed: Sep. 27, 1991

[30] Foreign Application Priority Data

Oct. 3, 1990 [JP] Japan ............... 2-104177[U]

[51] Int. Cl.$^5$ .......................... G01N 27/409
[52] U.S. Cl. .................. 204/426; 204/424; 204/427
[58] Field of Search ............ 204/424, 425, 426, 427

[56] References Cited

U.S. PATENT DOCUMENTS

| | | | |
|---|---|---|---|
| 4,798,693 | 1/1989 | Mase et al. | 264/44 |
| 4,861,456 | 8/1989 | Mase et al. | 204/425 |
| 4,983,271 | 1/1991 | Kato et al. | 204/426 |

FOREIGN PATENT DOCUMENTS 61-99051 6/1986 Japan .

Primary Examiner—John Niebling
Assistant Examiner—William T. Leader
Attorney, Agent, or Firm—Shea & Gould

[57] ABSTRACT

An oxygen sensor has an elongate plate form oxygen sensor element provided at a tip portion thereof with an oxygen detection portion which produces an electromotive force between electrodes or shows a variation in electrical resistance, according to the concentration of oxygen in a gas under measurement. The oxygen sensor element is composed of conductor portions each formed along the thickness direction of the oxygen sensor element so as to lead out a conductor lead provided in the oxygen sensor element to a surface of the oxygen sensor element. The oxygen sensor further has electrode terminal portions each provided on a surface of the oxygen sensor element so as to make conduction to the conductor lead through the conductor portion; contacts electrically connected to the electrode terminal portions of the oxygen sensor element; and a metallic container member containing the oxygen sensor element therein, wherein at least one of the conductor portions is located on the rear end side of contact point portions between the electrode terminal portions and the contacts.

13 Claims, 8 Drawing Sheets (b)

(c)

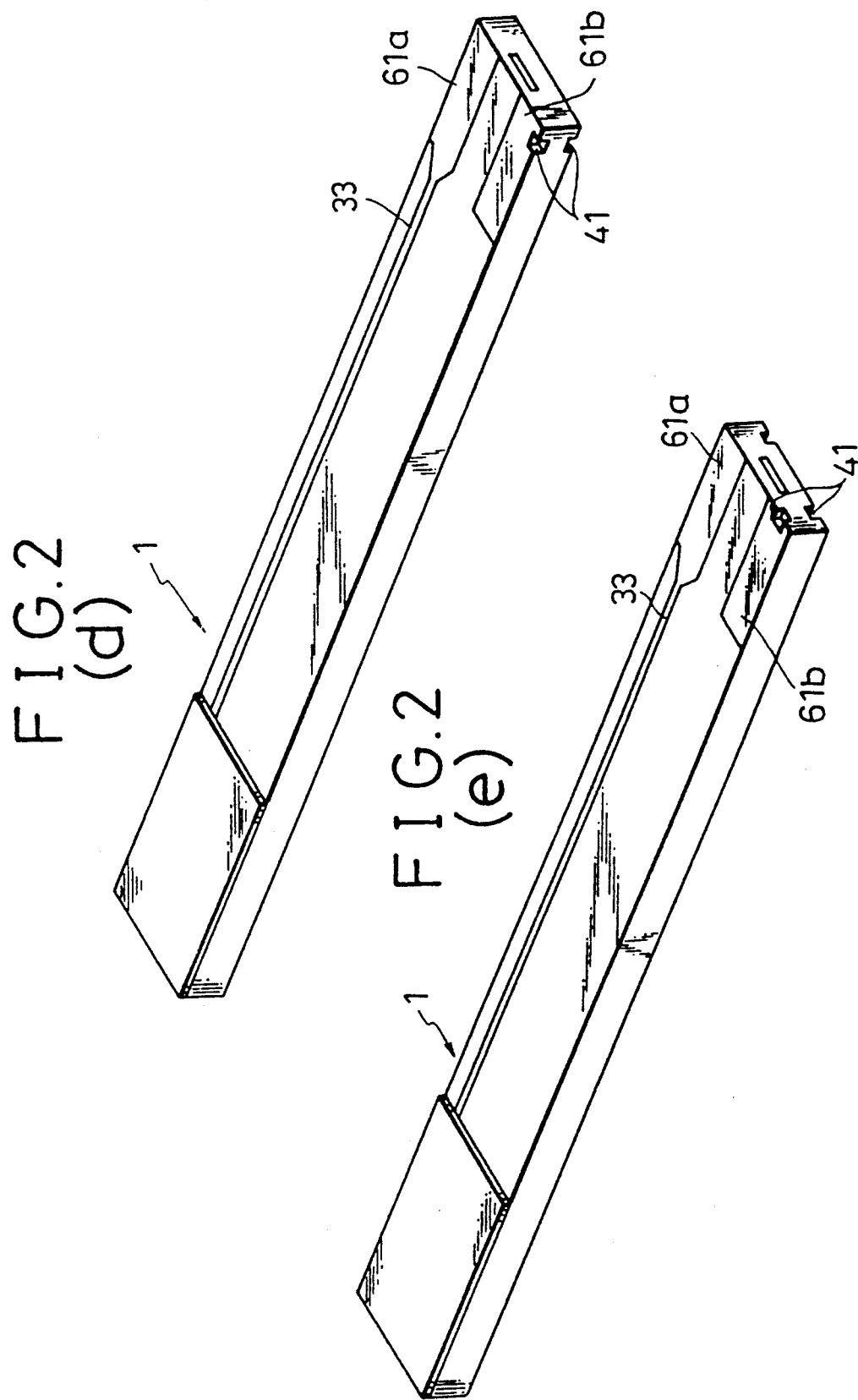

ary by a metallic housing 11 and a cylindrical metallic inner tube 12 welded thereto, through the action of talc 15 (15a and 15b) packed in the spaces between ceramic supporters 14 (14a, 14b and 14c). For protection of the oxygen sensor element 51 from external environments, a metallic outer tube 13 is fitted to the outer peripheral portion of an upper annular projection of the housing 11 and fixed in position by welding.
OXYGEN SENSOR

BACKGROUND OF THE INVENTION (1) Field of the Invention

This invention relates to an improvement in an oxygen sensor employing a plate form oxygen sensor element for detecting the concentration of oxygen in a gas under measurement, particularly an exhaust gas from an internal-combustion engine.

(2) Description of the Prior Art

As a so-called oxygen sensor, there has been known a system for detecting the concentration of oxygen in an exhaust gas from an internal-combustion engine and optimizing the combustion condition of the engine based on the detection signal, in order to achieve clarification of the exhaust gas, savings of fuel cost, etc.

In recent years, elongate plate form oxygen sensor elements have been proposed for use in the aforementioned oxygen sensor, from such viewpoints as ease of manufacture and ease of obtaining a compact design.

This type of oxygen sensor elements are constructed, for example, as shown in FIG. 6, in which a solid electrolyte capable of oxygen-ionic conduction and comprising zirconia as a main constituent is formed into an elongate plate-like shape, a measuring electrode 32 to be exposed to a gas under measurement is provided on a surface of an end portion of the thus formed solid electrolyte plates 31 (31a, 31b, 31c and 31d), whereas an inlet passage (in FIG. 6, represented by a cavity 43) for a reference gas (generally, the atmospheric air is used) opened at one end is formed in an oxygen sensor 51 along the longitudinal direction, and a reference electrode 34 is disposed at a depth portion of the reference gas inlet passage so as to face the measuring electrode 32. In addition to the electrodes 32 and 34, the oxygen sensor 10 may have an oxygen pumping electrode (not shown) or may have a heater 38 (FIG. 6) or the like, according to the intended use thereof.

For connection of the electrodes 32, 34 and the heater 38 to an external circuit, conductor leads (a conductor lead 33 for the measuring electrode, a conductor lead 35 for the reference electrode, and a conductor lead 39 for the heater) are provided extending from the electrodes 32, 34 and the heater 38 in the longitudinal direction of the oxygen sensor element 51. The conductor leads are so arranged as to reach electrode terminal portions 61 (61a, 61b, 61c and 61d) located near an end portion of the oxygen sensor element 51 on the side opposite to the side on which the aforementioned electrodes and the like are provided.

In order that lead wires 20 (FIG. 5) used for connection to an external circuit may be connected advantageously (with or without use of connectors), it is desirable that end portions of the conductor leads, on the side opposite to the side of the electrodes 32, 34 and the heater 38, be all disposed on the surface of the oxygen sensor element 51.

Therefore, the conductor leads making conduction to members disposed inside the oxygen sensor element 51, such as the reference electrode 34 and the heater 38, should be led out from the inside to the surface of the oxygen sensor element 51. This is accomplished, for example, by a method in which the conductor leads are led out to the surface of the oxygen sensor element 51 via through-holes 36 (36a, 36b and 36c) formed in the thickness direction of the oxygen sensor element 51.

Besides, in order to avoid needless lengthening of the conductor leads or to dispose the electrode terminal portions 61 as closer as possible to the rear end side (A-side) of the oxygen sensor element 51, the through-holes 36 have conventionally been located nearer to the front end (or tip) of the oxygen sensor element 51 than are the electrode terminal portions 61.

When the through-holes 36 are thus provided in the oxygen sensor element 51 formed mainly of a ceramic, however, the mechanical strength of the oxygen sensor element 51 at the portion of the through-holes 36 is lowered due to a reduction in the sectional area of the elongate plate form sensor element 51, a concentration of stress, etc.

This will be explained more in detail below.

FIG. 5 shows the construction of an oxygen sensor employing the oxygen sensor element 51 shown in FIG. 6. In FIG. 5, the oxygen sensor element 51 is held stationary by a metallic housing 11 and a cylindrical metallic inner tube 12 welded thereto, through the action of talc 15 (15a and 15b) packed in the spaces between ceramic supporters 14 (14a, 14b and 14c). For protection of the oxygen sensor element 51 from external environments, a metallic outer tube 13 is fitted to the outer peripheral portion of an upper annular projection of the housing 11 and fixed in position by welding.

In the construction of the oxygen sensor, the contacts 16 are pressed against the electrode terminal portions 61 with a pressure not lower than a predetermined value, at contact point portions between the electrode terminal portions 61 and the contacts 16. Therefore, there is only a low degree of freedom between the oxygen sensor element 51 and a contact member 26. Thus there has been the problem that when an excessive bending moment is exerted on the portion of the oxygen sensor element 51 above the top surface of the talc 15b in assembling the oxygen sensor or in other situations, a bending moment is exerted also on the portion of the through-holes 36, which is relatively lower in mechanical strength, resulting in breakage of the sensor element at that portion.

There has also been the problem that an excessive external shock exerted on the oxygen sensor 10 may vibrate the contact member 26, the mass of which is somewhat large, whereby a bending moment is exerted on the oxygen sensor element 51, resulting in breakage of the sensor element at the portion of the through-holes 36, similarly to the above case.

Referring now to FIG. 3, there are shown a schematic view and a moment diagram representing the condition where a moment and a load are simultaneously exerted on the contact point portion. As is clear from FIG. 3, a bending moment acts also on the through-hole position, where the mechanical strength is relatively lower, so that the element may be broken at the portion of the through-holes 36.

SUMMARY OF THE INVENTION

This invention contemplates a solution to the aforementioned problems involved in the prior art.

It is accordingly an object of this invention to provide an oxygen sensor which is free from the possibility that a bending moment may be exerted on a mechanically weaker portion of an oxygen sensor element thereof, and which is therefore prevented from breakage of the oxygen sensor element during the assemblage or use thereof or in other situations.

According to this invention, there is provided an oxygen sensor comprising:

an elongate plate form oxygen sensor element provided at a tip portion thereof with an oxygen detection portion which produces an electromotive force between electrodes or shows a variation in electrical resistance, according to the concentration of oxygen in a gas under measurement, the oxygen sensor element comprising conductor portions each formed along the thickness direction of the oxygen sensor element so as to lead out a conductor lead provided in the oxygen sensor element to a surface of the oxygen sensor element, and electrode terminal portions each provided on a surface of the oxygen sensor element so as to make conduction to the conductor lead through the conductor portion;

contacts electrically connected to the electrode terminal portions of the oxygen sensor element; and a metallic container member containing the oxygen sensor element therein, wherein at least one of the conductor portions is located on the rear end side of contact point portions between the electrode terminal portions and the contacts.

Provided with the aforementioned construction, the oxygen sensor of this invention is free from the possibility of a bending moment being exerted on a through-hole portion of an oxygen sensor element, during the assemblage or use of the sensor or in any other situation. It is therefore possible, by this invention, to provide an oxygen sensor which is strong enough to resist external shocks and the like and is free from the possibility of breakage of an oxygen sensor element thereof.

The above and other objects, features and advantages of this invention will become apparent from the following description and appended claims, taken in conjunction with the accompanying drawings.

DESCRIPTION OF PREFERRED EMBODIMENTS

This invention will now be explained more in detail with reference to some preferred embodiments thereof, which are not to be construed as limiting the invention.

Figure 1:
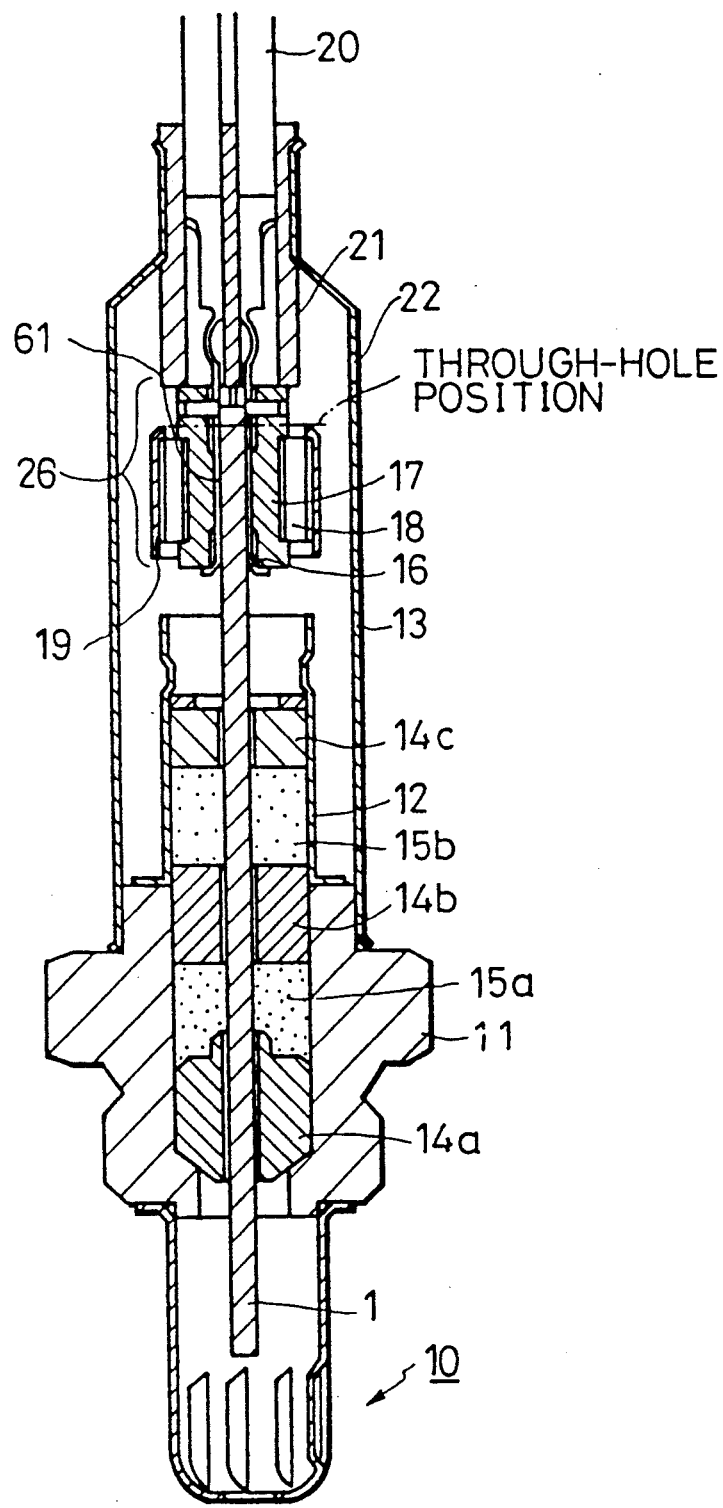
FIG. 1 is a schematic sectional view showing the construction of one embodiment of the oxygen sensor according to this invention.
Figure 2:
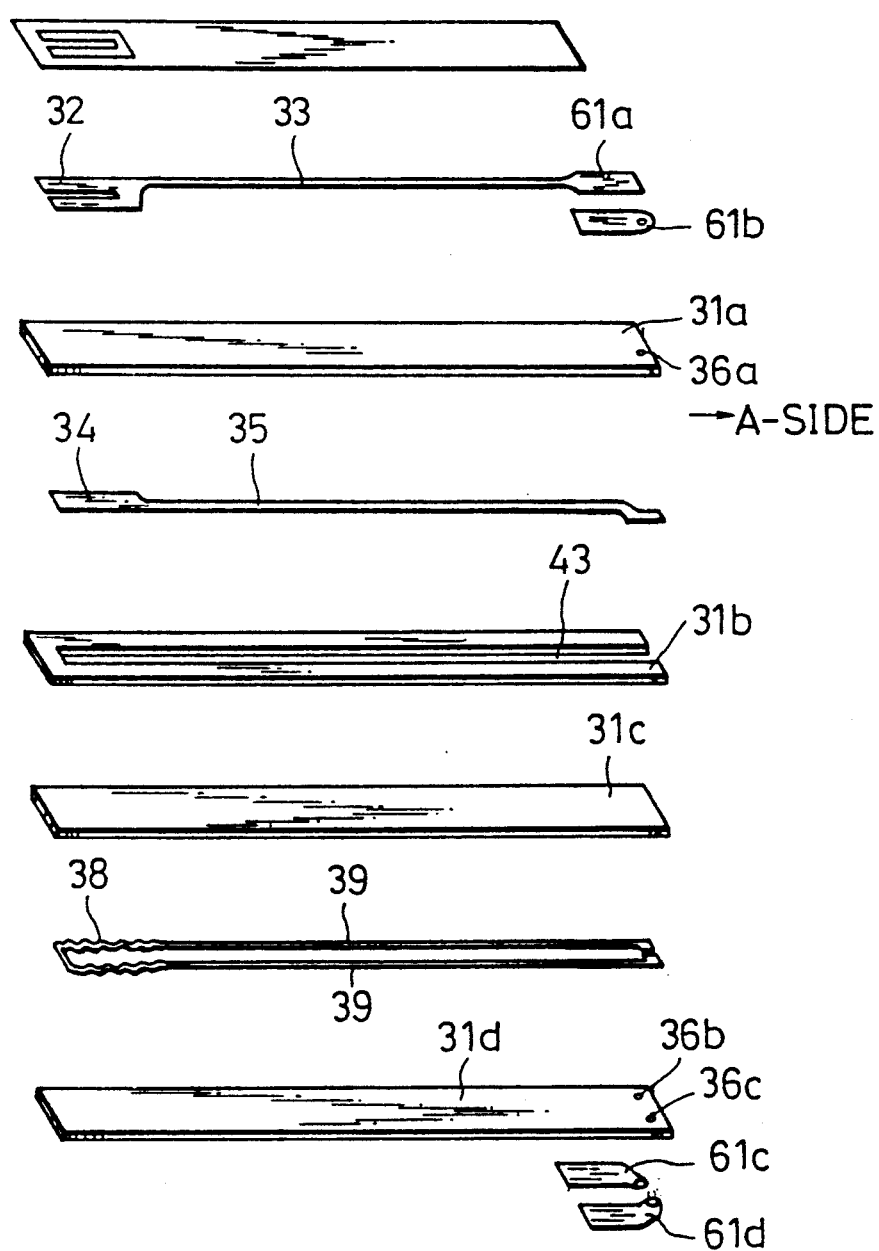
FIG. 2(a) is an exploded diagrammatic view showing one embodiment of the oxygen sensor element according to this invention.
FIG. 2(b) is a sectional view showing the construction of a through-hole portion of the oxygen sensor element of FIG. 2(a)
FIG. 2(c) is a sectional view showing another embodiment of the conductor portion in this invention.
FIGS. 2(d) and 2(e) are each a perspective view showing a further embodiment of the conductor portion in this invention.
Figure 2:
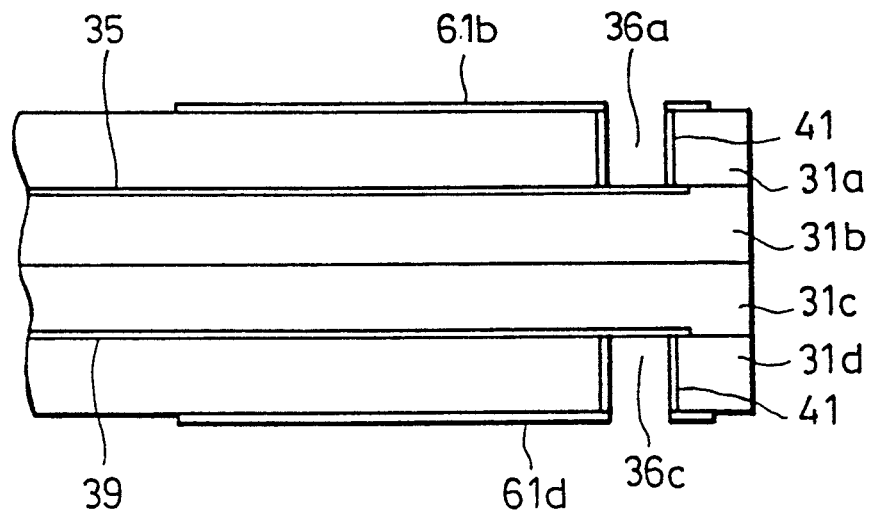
Figure 2:
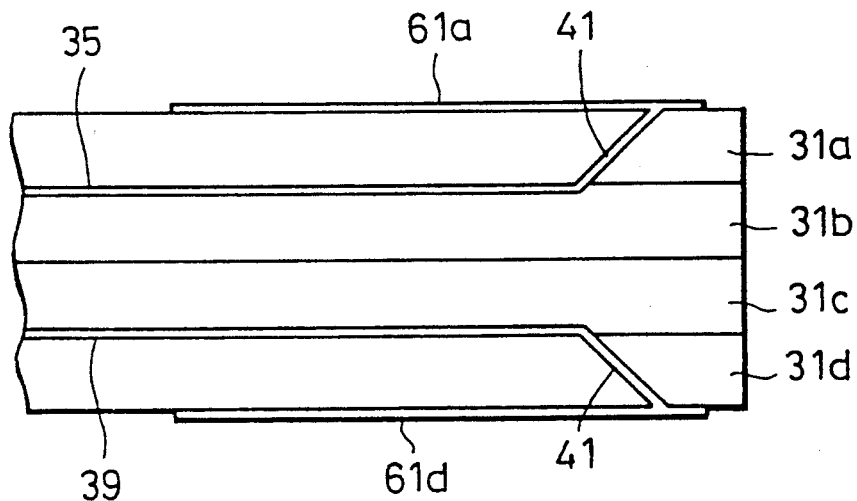

FIGS. 1 and 2(a) respectively show a sectional view of an oxygen sensor and an exploded diagrammatic view of an oxygen sensor element, according to one embodiment of this invention.

In FIG. 1, a plate form oxygen sensor element 1 is held stationary by a metallic housing 11 and a cylindrical metallic inner tube 12 welded thereto, through the action of talc 15 (15a and 15b) packed in the spaces between ceramic supporters 14 (14a, 14b and 14c), and is sealed airtight.

For protection of the oxygen sensor element 1 from external environments, a metallic outer tube 13 is fitted to the outer peripheral portion of an upper annular projection of the housing 11 and fixed in position by welding. On the other hand, a rubber stopper 21 with lead wires 20 piercing therethrough is fastened by caulking the outer tube 13, on the side of an opening end at an upper position, in the figure, opposite to the side of engagement with the housing 11. The atmospheric air, as a reference gas required for the oxygen sensor element 1, is taken in through a vent 22 opened in the side surface of the outer tube 13.

As shown by the exploded diagrammatic view in FIG. 2(a), the oxygen sensor element 1 has a laminate structure comprising plates 31 (31a, 31b, 31c and 31d) of a solid electrolyte capable of oxygen-ionic conduction (such a plate will be hereinafter referred to as "solid electrolyte plate"). The solid electrolyte plate 31b has a cavity 43 cut therein longitudinally, for feeding the atmospheric air to a reference electrode 34. On the upper surface of the uppermost solid electrolyte plate 31a, a measuring electrode 32 is deposited on one end portion (a left end portion in the figure), and a conductor lead 33 for the measuring electrode 32 is formed between the measuring electrode 32 and the right end, in the figure, of the solid electrolyte plate 31a.

On the lower surface of a left end portion, in the figure, of the solid electrolyte plate 31a is deposited the reference electrode 34, which faces the aforementioned measuring electrode 32. A conductor lead 35 for the reference electrode 34 is also formed on the lower surface of the solid electrolyte plate 31a.

A right end portion, in the figure, of the solid electrolyte plate 31a is provided with a through-hole 36a in the thickness direction of the solid electrolyte plate 31a.

The inner peripheral surface of the through-hole 36a is coated with a conductor portion 41, as shown in FIG. 2(b). The conductor portion 41 makes contact both with the right end (in the figure) of the reference electrode conductor lead 35 provided on the lower side of the solid electrolyte plate 31a and with the right end (in the figure) of the electrode terminal portion 61b provided on the upper side of the solid electrolyte plate 31a. As a result, the reference electrode conductor lead 35 is led out from the inside to the surface of the oxygen sensor element 1 by the conductor portion 41.

Similarly, heater conductor leads 39 provided in the inside of the oxygen sensor element 1 are brought into contact with the electrode terminal portions 61c and 61d, and hence led out to the surface of the oxygen sensor element 1, by conductor portions 41 formed, by coating, on the inner peripheral surfaces of through-holes 36b and 36c bored in the solid electrolyte plate 31d.

The through-holes 36 are located on the rear end side (A-side in the figure) of contact point portions at which the electrode terminal portions make contact with contacts 16 for electric conduction.

Figure 3:
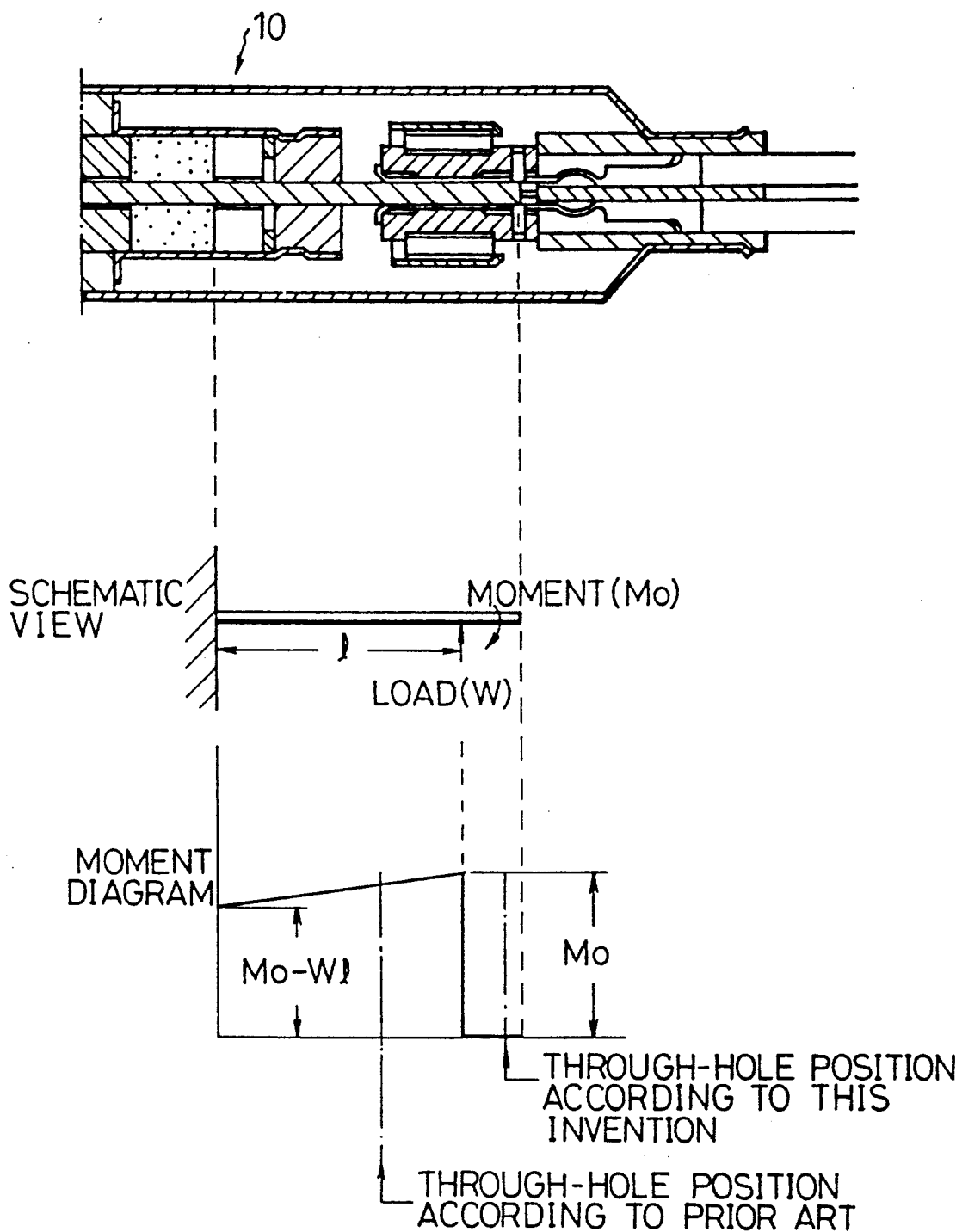
FIG. 3 shows a schematic view and a moment diagram representing the condition where a moment and a load are simultaneously exerted on a contact point portion.

In the oxygen sensor constructed as above, the electrode terminal portions 61 of the oxygen sensor element 1 are electrically connected to the contacts 16 under a spring force applied by a presser spring 18 through a ceramic housing 17. The spring force exerted by the presser spring 18 is set at or above a predetermined value, and, accordingly, there is only a low degree of freedom between the oxygen sensor element 1 and a contact member 26 comprising the contacts 16, ceramic housing 17, presser spring 18 and a caulking ring 19. Therefore, an external shock or the like may cause a bending moment to be exerted on that portion of the oxygen sensor element 1 which is above the upper surface of the talc 15b. However, the through-holes 36, which are the cause of a relatively lower mechanical strength, are located on the rear end side (A-side in the figure) of the points of contact between the electrode terminal portions 61 of the oxygen sensor element 1 and the contacts 16, and no bending moment is exerted on the portion where the through-holes 36 are provided, as clearly seen from the moment diagram in FIG. 3. Consequently, the oxygen sensor element 1 is prevented from being broken at the portion of the through-holes 36.

Although the above embodiment has been described with reference to the case where through-holes are provided as means for leading out the conductor leads 35 and 39 from the inside to the surface of the oxygen sensor element 1, a construction as shown in FIG. 2(c) may be adopted in which cuts are provided in the oxygen sensor element 1 and conductors portions 41 are provided along the cuts by coating or the like so that the conductor leads 35 and 39 are led out to the surface of the oxygen sensor element 1 through the conductor portions 41.

Also applicable are constructions as shown in FIGS. 2(d) and 2(e), in which conductor portion 41 extend to a side surface or an upper end portion of the oxygen sensor element 1.

Figure 4:
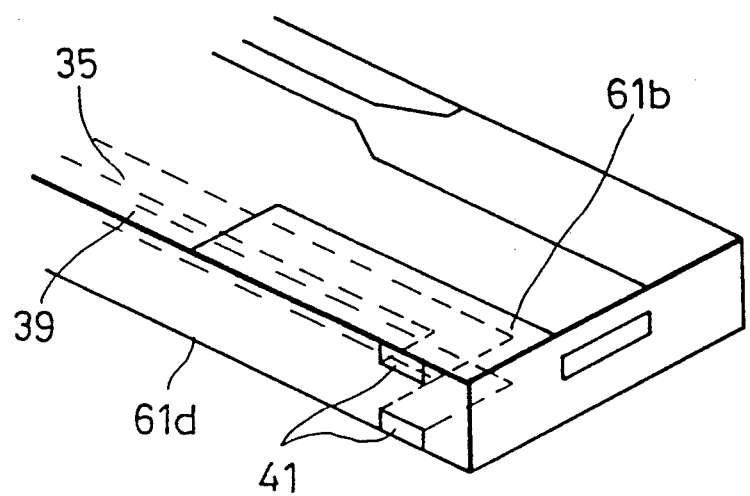
FIGS. 4(a) and 4(b) are each a perspective view showing a further embodiment of the conductor portion in this invention.
Figure 4:
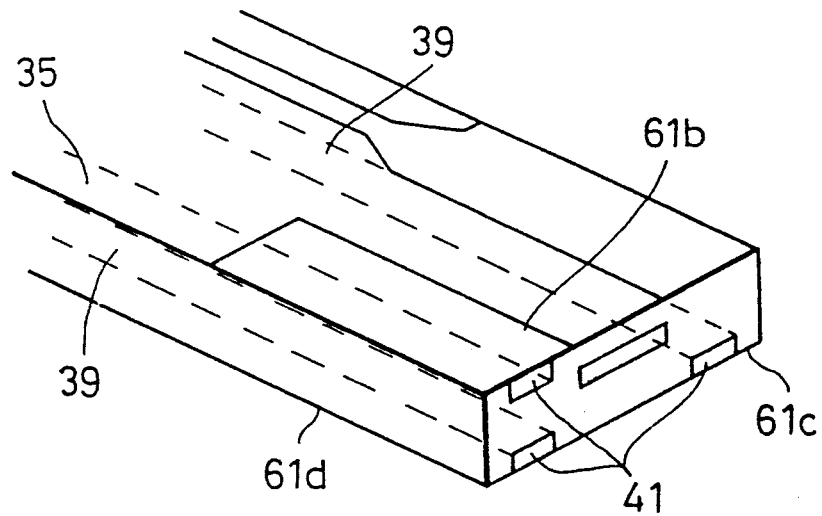
Figure 5:
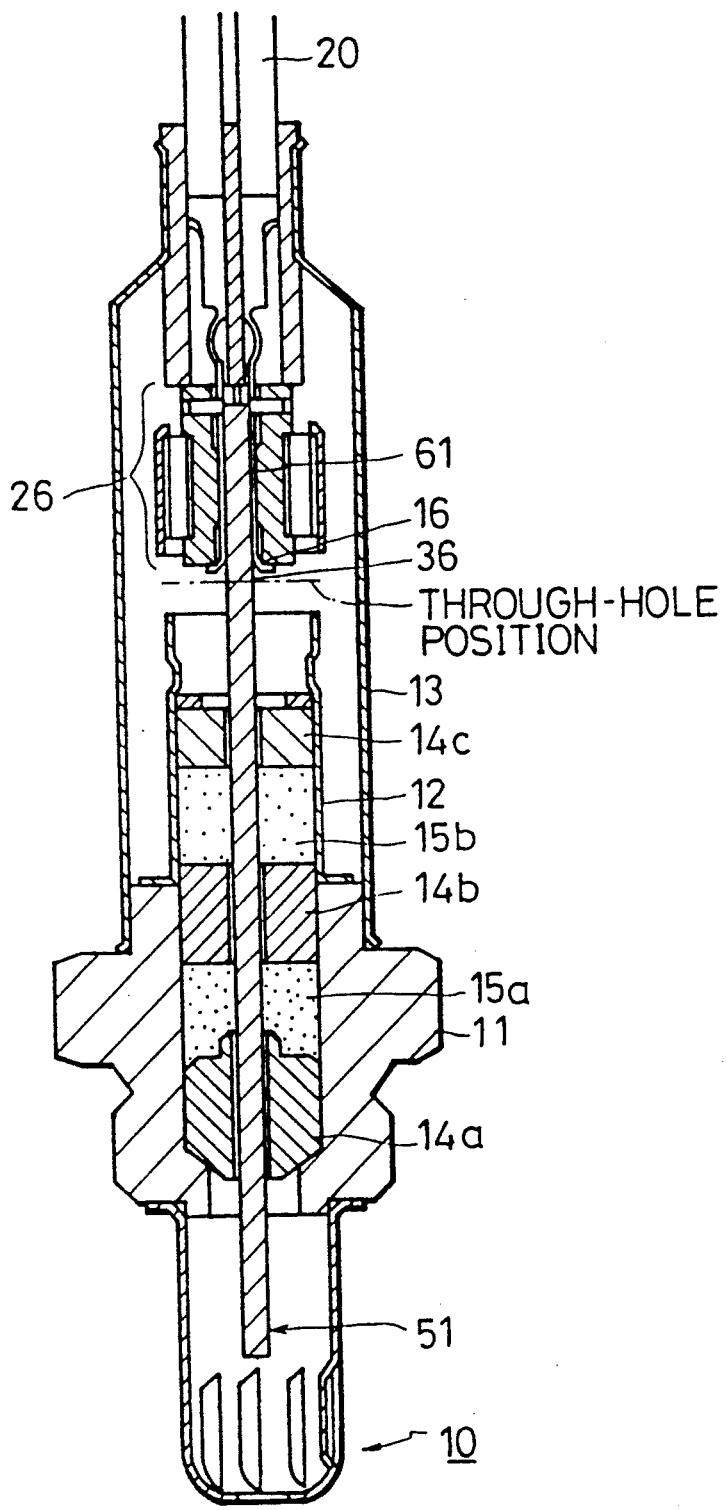
FIG. 5 is a schematic sectional view showing an oxygen sensor according to the prior art.
Figure 6:
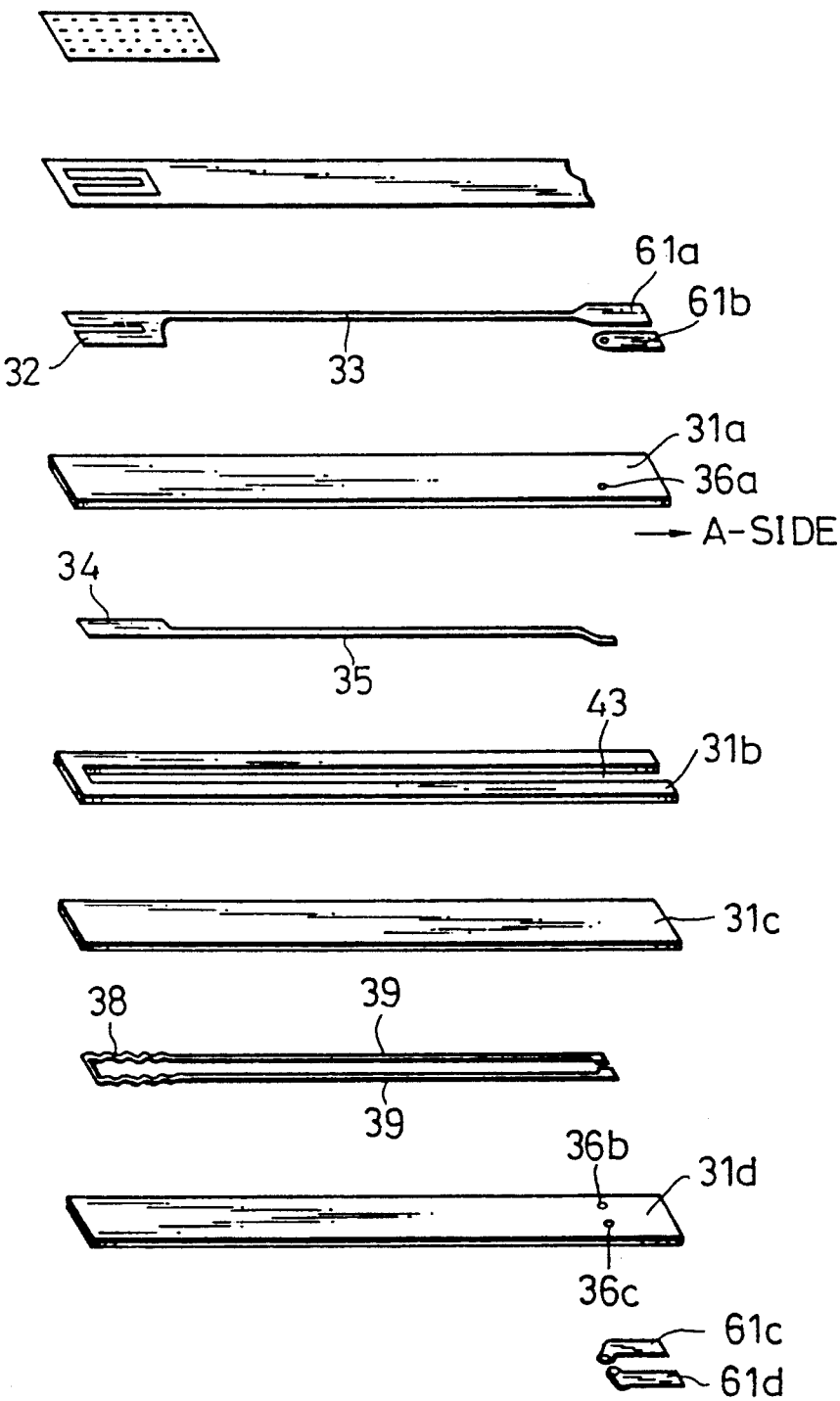
FIG. 6 is an exploded diagrammatic view showing an oxygen sensor element according to the prior art.

As shown in FIG. 4(a), furthermore, conductor leads 35 and 39 exposed on a side surface of the oxygen sensor element 1 may be electrically connected to electrode terminal portions 61b and 61d on the surface of the oxygen sensor element 1 by conductor portions 41 formed by applying a conductive material to the side surface of the oxygen sensor element 1. Moreover, as shown in FIG. 4(b), conductor leads 35 and 39 may be exposed on an upper end surface of the oxygen sensor element 1 and be electrically connected to electrode terminal portions 61b, 61c and 61d by conductor portions 41 formed by applying a conductive material to the upper end surface of the oxygen sensor element 1.

The effect obtained according to this invention is maximized when all of the through-holes 36 (36a, 36b, and 36c) in the oxygen sensor element 1 are located on the rear end side of the contact point portions between the electrode terminal portions 61 and the contacts 16. However, locating at least one of the through-holes 36 on the rear end side of the contact point portions is sufficient to produce a preferable effect, as compared with the prior art.

Besides, although the oxygen sensor element in the above embodiment has been described as not having an oxygen pumping electrode, this invention is also applicable to oxygen sensor elements which have oxygen pumping electrodes.

Furthermore, it will be readily understood by those skilled in the art that this invention is also applicable to oxygen sensors which comprise lead portions and conductor portions and which utilize variations in electrical resistance.

As is clear from the above descriptions, according to the oxygen sensor of this invention, conductor portions formed in the thickness direction of an oxygen sensor element so as to lead out conductor leads from the inside to the surface of the oxygen sensor element are disposed on the rear end side of contact point portions between electrode terminal portions and contacts. This construction has the advantage that no bending moment is exerted on the conductor portions, which are relatively lower in mechanical strength, of the oxygen sensor element that the oxygen sensor element is prevented from being broken at the portion of the conductor portions.

What is claimed is:

1. In an oxygen sensor including an elongate plate form oxygen sensor element, the oxygen sensor element having an oxygen tip portion provided with electrodes for detecting the concentration of oxygen in a gas under measurement; a distal end portion for connecting said oxygen sensor element to an external circuit; conductor leads arranged inside said element and connected to said electrodes and extending from said tip portion to said distal end portion; electrode terminals provided on a surface of said element at said distal end portion, each of said terminal portions having a first front end and a second rear end and arranged such that the first front end is located nearer the oxygen tip portion of the oxygen sensor than the second rear end; and conductor portions for connecting said conductor leads to said electrode terminals; the improvement wherein at least one of said conductor portions connects a conductor lead to an electrode terminal at said second rear end of the terminal.

2. The oxygen sensor as set forth in claim 1, wherein at least one of the conductor portions is provided along a through-hole formed in the thickness direction of the oxygen sensor element.

3. The oxygen sensor as set forth in claim 1, wherein at least one of the conductor portions is provided along a cut formed in the oxygen sensor element.

4. The oxygen sensor as set forth in claim 1, wherein at least one of the conductor portions extends to a side surface of the oxygen sensor element.

5. The oxygen sensor as set forth in claim 1, wherein at least one of the conductor portions extends to an upper end portion of the oxygen sensor element.

6. The oxygen sensor as set forth in claim 1, wherein at least one of the conductor leads is exposed on a side surface of the oxygen sensor element and the conductor portion for the conductor lead is provided on the side surface by application of a conductive material.

7. The oxygen sensor as set forth in claim 1, wherein at least one of the conductor leads is exposed on an upper end surface of the oxygen sensor element and the conductor portion for the conductor lead is provided on the upper end surface by application of a conductive material.

8. The oxygen sensor as set forth in claim 1, wherein all of the conductor portions connect conductor leads to said electrode terminals at said second rear end of the terminal.

9. The oxygen sensor as set forth in claim 1, further comprising a heater.

10. A sensor for use in sensing oxygen and generating an output signal over lead wires representative of the concentration of oxygen within a sample, the sensor comprising:

an elongated oxygen sensing element;
a lower housing member, enclosing a lower portion of said elongated oxygen sensor element, for holding said sensing element in a stationary position, wherein a top portion of said lower housing member forms an annular projection;
an inner tube, enclosing a middle portion of said elongated oxygen sensing element, having a plurality of supports enclosing said elongated oxygen sensing element for holding said sensing element in the stationary position within said lower housing member;
an outer tube coupled to an outer peripheral portion of the annular projection of said lower housing member and enclosing at least a portion of said elongated oxygen sensing element; and
an upper housing member, coupled to a top portion of said outer tube, for holding the lead wires in a stationary position, said upper housing member further enclosing an upper portion of said elongated oxygen sensing element;
wherein said elongated oxygen sensing element has at least one conductor portion for facilitating connection between said sensing element and the lead wires, said at least one conductor portion being located at the top edge portion of said elongated oxygen sensing element.

11. The sensor of claim 10, wherein said upper housing member comprises:

contracts connected to the lead wires;
a ceramic housing enclosing the upper portion of said elongated oxygen sensing element and said contacts; and
a presser spring for applying a spring force to said ceramic housing so as to electrically connect said elongated oxygen sensing element to the lead wires through said contacts.

12. The sensor of claim 11, wherein said outer tube has a vent opening that allows exhaust gas from an internal-combustion engine to serve as a sample for the sensor.

13. The sensor of claim 10, wherein said conductor portion comprises a plurality of through-holes located at the top edge portion of said elongated oxygen sensing element.

* * * * *